United States Patent [19]
Brus et al.

[11] 4,448,524
[45] May 15, 1984

[54] REFLECTIVE CONTAINMENT OF ELECTROMAGNETIC RADIATION IN MATRIX ISOLATION THIN FILMS

[75] Inventors: Louis E. Brus, Madison; Ronald Rossetti, North Plainfield, both of N.J.

[73] Assignee: Bell Telephone Laboratories, Incorporated, Murray Hill, N.J.

[21] Appl. No.: 301,888

[22] Filed: Sep. 11, 1981

Related U.S. Application Data

[63] Continuation of Ser. No. 120,689, Feb. 11, 1980, abandoned.

[51] Int. Cl.³ .................. G01N 1/28; G01N 21/01; G02B 5/14
[52] U.S. Cl. .................. 356/36; 350/96.12; 356/244; 356/318; 356/432
[58] Field of Search .................. 356/36, 51, 244, 318, 356/432; 350/96.12, 96.17

[56] References Cited

U.S. PATENT DOCUMENTS

| | | | |
|---|---|---|---|
| 3,431,411 | 3/1969 | Harrick | 250/339 |
| 3,436,159 | 4/1969 | Harrick et al. | 356/51 |
| 3,674,337 | 7/1972 | Marcatili | 350/96.17 |
| 3,947,087 | 3/1976 | Furuta et al. | 350/96.12 |
| 4,040,749 | 8/1977 | David et al. | 356/73.1 |
| 4,181,441 | 1/1980 | Noller | 356/414 |

FOREIGN PATENT DOCUMENTS 46-38399 11/1971 Japan .................. 356/432

OTHER PUBLICATIONS

Ulrich et al., "Planar Leaky Light-Guides & Couplers" App. Physics, vol. 1, 1973, pp. 55-68.
Y. Levy, C. Imbert, J. Cipriani, S. Racine and R. Dupeyrat, "Raman Scattering of Thin Films as a Waveguide", Optics Communications, vol. 11, No. 1, May 1974, pp. 66-69.
S. C. Rashleigh, "Positive-Permittivity-Metal Cladding: Its Effect on the Modes of Dielectric Optical Waveguides", Applied Optics, vol. 15, No. 11, Nov. 1976, pp. 2804-2811.
A. K. Mal'tsev, R. G. Mikaelyan and O. M. Nefedov, "A Cryostat for Studying Chemical Reactions by the Method of Matrix Confinement", Cryogenics, vol. 10, Apr. 1972, pp. 147-148.

*Primary Examiner*—William H. Punter
*Attorney, Agent, or Firm*—Walter G. Nilsen

[57] ABSTRACT

Efficient transmission of light through a matrix isolation thin film is obtained despite the fact that the index configuration of the thin film is not appropriate for classical waveguides. The light is transmitted through the film approximately parallel to the substrate, thereby permitting analysis of the thin film, stimulation of reaction within the thin film, or use of the thin film as an optical memory.

18 Claims, 6 Drawing Figures

REFLECTIVE CONTAINMENT OF ELECTROMAGNETIC RADIATION IN MATRIX ISOLATION THIN FILMS

This is a continuation of application Ser. No. 120,689, filed Feb. 11, 1980, and now abandoned.

BACKGROUND OF THE INVENTION

1. Field of the Invention

This invention involves matrix isolation thin films and the reflective containment of electromagnetic radiation in such films for purposes such as spectroscopic studies of the film material, and the stimulation of reactions between various film constituents.

2. Description of the Prior Art

Over the past century, spectroscopic techniques have provided invaluable information on the detailed structure of atoms and molecules and their various interactions. Atoms and small molecules may be studied relatively easily while in the vapor state, and under certain circumstances, even in the solid state. Under these experimental conditions, the spectra associated with systems under study are sufficiently clear to be analyzed in detail thereby yielding important information on the physical characteristics of the systems under study. However, more complicated molecules, of larger size or of sophisticated structure, yield highly involved spectra whose analysis becomes more and more difficult, and for certain systems impossible, even with the use of sophisticated computer instrumentation. The spectra of such systems are complicated not only by the inherently detailed nature of the spectra of the individual molecules, but are further complicated by spectral characteristics associated with thermal motion and interactions between various groups of molecules.

During the past twenty-five years, the field of matrix isolation spectroscopy has developed into a powerful tool to analyze complicated, or highly reactive, molecular systems. The matrix isolation technique generally involves freezing, in the form of a thin film, a rarefied mixture of the material to be studied and an inert gas. The frozen thin film of this mixture is then analyzed using basic prior art optical techniques, e.g., exposure of the sample to irradiating electromagnetic radiation, and analysis of the resultant transmitted or scattered light. In this matrix configuration, the spectroscopic effects of thermal motion are essentially removed by virtue of the very low temperature of the frozen sample, e.g., on the order of 4 degrees Kelvin, or as low as possible. Furthermore, on a microscopic scale, the frozen sample appears as isolated molecules of the substance to be studied, frozen in the inert gas which acts as a host lattice. In this configuration, the molecules can be studied as isolated entities, thereby minimizing the spectroscopic complications associated with interactions between the guest and its environment (hence, the term "matrix isolation").

The thin films of the guest-host mixture are produced by directing a stream of appropriate guest-host vapor toward a cold substrate. The resultant thin film forms a guest-host lattice amenable to spectroscopic analysis. The irradiating light is directed towards the thin film and the resultant scattered light may be studied, or the transmission through the thin film may be analyzed, to obtain spectroscopic information relating to the molecules under study. Practical film sizes, however, are on the order of 100 microns, and light, either scattered off the 100 micron film or transmitted through the 100 micron film, yields only a very small signal, which must be treated with sophisticated electronics before it can provide meaningful information. Many systems are not amenable to analysis by matrix isolation spectroscopy because of the very small signal which is obtained. Various techniques are constantly being suggested to increase signal levels associated with matrix isolation spectroscopy, but none of these have yielded the type of improvement which would expand significantly the number of systems amenable to the matrix isolation technique.

In a totally unrelated art, thin films have been suggested as appropriate media for waveguide transmission of optical and infrared electromagnetic energy. Associated work has proposed the use of optical fibers as waveguides, and fiber lightguides have developed into the primary long distance optical transmission medium. However, interest in thin film waveguides has persisted since they are more readily used in integrated optical circuitry. The thin film waveguide generally comprises a center region where most of the optical radiation is transmitted, and outer regions of lower index of refraction where progressively less electromagnetic radiation is transmitted. This variation in index of refraction is fundamentally responsible for the guiding nature of the thin film. Significant efforts have been expended in learning how to fabricate films with appropriate index of refraction configurations so as to enhance the waveguiding properties of the thin film.

The development of thin film waveguide technology for use in information transmission systems has stimulated the use of such waveguides in experimental research directed toward the study of materials through optical means. Exemplary of this area of study is an article by Y. Levy, et al, in *Optics Communications* Vol. 11, No. 1 at page 66. These authors suggest studying various materials by forming a thin film waveguide of the material under study, irradiating the thin film waveguide with appropriate optical radiation which is sent through the film in various waveguide modes, and studying the resultant raman scattered light. It must be emphasized, however, especially with a view toward the invention described in this application, that work, such as that described by Levy, et al, depends on the formation of a "classical" thin film waveguide. Specifically, the thin film must have associated with it a core region of higher index of refraction than the surrounding "cladding" regions. (The prism device employed by these authors, which couples the probing laser into the waveguide mode, functions only when such a "classical" waveguide structure is used.)

SUMMARY OF THE INVENTION

This invention is a new technique for propagating light through frozen matrix isolation films. In the inventive technique, the guest-host material is formed into a film as in prior art matrix isolation techniques. However, in the inventive technique, the index of refraction configuration is not adequate to form a "classical waveguide". Nevertheless, irradiating light is transmitted through the thin film along a direction approximately parallel to the substrate to increase the interactive distance over which the thin film is exposed to the analyzing light. Since thin films used in matrix isolation spectroscopy generally have very low indices of refraction, it is usually impossible to find a supporting substrate with a lower index of refraction than the film, which would be necessary to form the cladding in a "classical" thin film waveguide. Nevertheless, applicants have shown that even in the inventive "nonwaveguide" configuration, structures can be devised which cause sufficient guiding of the inserted light to allow for at least a centimeter or two of propagation, thereby increasing the interactive distance by approximately two orders of magnitude over that previously obtained in matrix isolation spectroscopy.

Since the thin film in this technique does not provide significant "guiding" as in a classical waveguide, the exact light injection technique and direction of lightwave propagation through the film becomes more important. In the inventive technique, the propagation of light through the thin film may be enhanced by carefully launching the light into the thin film so as to insure that the light will be transmitted substantially parallel to the substrate surface. Such improved launching techniques include the fabrication of a smooth frozen gas film face perpendicular to the substrate. Light launched into this face along a direction parallel to the substrate is only minimally deflected during launching into the film.

While the propagation techniques discussed here will be used primarily for optical analysis of the film, they may be used equally well to stimulate chemical reactions among the matrix constituents, by exposure to appropriate radiation transmitted through the matrix. The reaction may be stimulated by absorption of radiation from the lightbeam. Such absorption may directly stimulate appropriate reactions or may form species which then react with other film constituents. Such reactions occurring at low temperature between molecules held in specific relative orientations often yield unique products as compared with conventional chemical synthesis methods. In addition, in the matrix isolation apparatus these reactions may exhibit isotopic specificity if the absorption spectrum of the absorbing molecule is isotopically resolved. Reactions in matrix isolation thin films may be used as a new synthesis method. Products of thin film reactions may be detected by allowing the film to warm and analyzing the emitted vapors, or by studying the film with lightbeams propagating through the film subsequent to, or simultaneously with, the reaction initiating lightbeam. Recent suggestions involving the use of thin films as optical memories could take advantage of the inventive technique.

DETAILED DESCRIPTION

Figure 1:
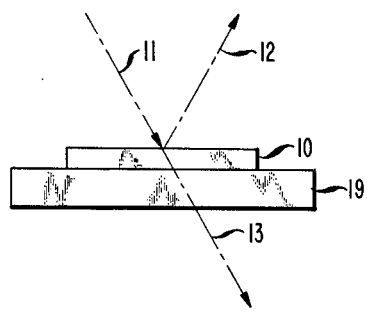
FIG. 1 is a schematic representation of the prior art matrix isolation spectroscopy technique.

FIG. 1 is a schematic representation of the prior art matrix isolation spectroscopy technique. In this FIG., 10 is a frozen sample of guest molecules in an appropriate inert host lattice. The frozen sample is formed on a substrate 19. 11 is impinging radiation of frequency appropriate to the guest molecule under study. 12 is scattered light, and 13 is transmitted light, both of which may contain information regarding the structure of the guest molecule under study.

While the film in FIG. 1 may be on the order of centimeters *long*, it is usually only on the order of 100 microns *thick*. Consequently, the light beam 11 interacts with the film 10 only over a very small distance. Therefore, signals carried by the scattered light 12 or transmitted light 13 are very small, limiting the usefulness of the matrix isolation technique.

Figure 2:
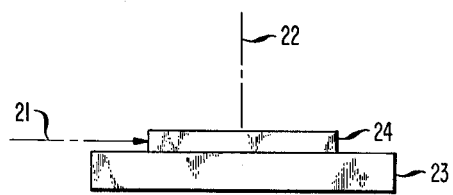
FIG. 2 is a schematic representation of the inventive technique.

FIG. 2 is a schematic representation of the inventive matrix isolation light propagation technique. In an embodiment of this technique, impinging radiation 21 enters the frozen guest-host thin film in a direction approximately perpendicular to an axis, 22, along the film's thinnest dimension (i.e., the radiation is launched parallel to the substrate, 23).

Prior art analysis techniques in fields other than matrix isolation spectroscopy have increased signal strength by transmitting light through a thin film in a waveguide mode along a direction parallel to the substrate surface. It is important to recognize the theoretical and practical differences between the waveguiding phenomenon exhibited in these prior art techniques and the containment of light exhibited in this invention. The prior art waveguide phenomenon depends upon the index differences between the core and the cladding regions of the waveguide. The core region must have an index of refraction greater than that of the cladding. In appropriate waveguide configurations, light is transmitted through the waveguide with a theoretical 100% guiding efficiency. The waveguide may be graded or may involve discrete index boundaries, but in all instances, the proper index configuration is an absolute prerequisite, i.e., at least one index of refraction value in the core must be greater than at least one index of refraction value in the cladding.

This invention does not have an index of refraction configuration appropriate for a classical waveguide. Although this invention may involve dielectrics with a discrete index of refraction discontinuity, the index configuration will be reversed from that required in "classical optical waveguides", namely, in this invention light will be transmitted in a region of lower index than that of a bounding medium. Alternatively, this invention may involve a dielectric/metal boundary. (In the context of this specification, the term "metals" includes all substances which have complex dielectric coefficients, as opposed to materials such as dielectrics which have substantially real dielectric coefficients.)

This invention is not a classical waveguide. It rather depends upon partial reflection at an index boundary. Such reflection is well-known in electromagnetic theory. In this invention, every reflection at the substrate boundary results in some loss of light and in some containment of light. Applicants find that with proper design, the reflection at the substrate boundary may be sufficient to yield significant containment of the light over distances of a centimeter or two. To distinguish this type of transmission from the prior art classical waveguide, applicants refer to their invention as "reflective containment" of light within a thin film, as opposed to classical waveguiding of light within a thin film.

Insertion of light into a classical waveguide may be effected by a number of techniques, some of which may be used in the inventive thin film technique, although the invention relies upon reflective containment rather than waveguiding. In a classical waveguide, light may be injected into a waveguide mode using "classical" prism or grading techniques which match the light wavevector to that of the desired waveguide mode. If the film thickness D is approximately the same size as the wavelength $\lambda$, then the film supports only a few transverse modes. Under such cicumstances, a tunable wavelength experiment becomes difficult, since the injection angle depends upon wavelength. In addition, the incident light flux must be limited since frozen gas films have relatively low laser intensity damage thresholds. However, if $\lambda/D$ is on the order of $10^{-2}$, the light beam does not have to be as tightly focused, the incident damage intensity threshold is greatly increased, and simplified coupling devices may be used. In this limit the most efficient injection technique involves simply focusing the light source, usually a laser, upon a polished thin film end through a surface perpendicular to th propagation direction. Although in the inventive process the film does not form a "classical waveguide", the inventive process may involve such an injection technique.

The invention considers two specific embodiments to yield reflective containment. The first of these embodiments involves a matrix film supported on a metallic mirror. A lightbeam propagating down the film will be reflected by total internal reflection at the matrix gas interface (the critical angle of incidence is about 51 degrees for visible wavelengths) and by grazing angle metallic reflection at the matrix-mirror interface. Propagation lengths of several centimeters are possible in these structures.

This embodiment is effective for low intensity levels such as would be encountered in a measurement of an absorption spectrum with incoherent light. However, at high intensity levels absorption of light by the metallic surface can produce enough heat to damage the frozen gas film. The intensity damage threshold of metallic mirrors might be increased by coating the bare metal with an approximately one micron thick layer of hard transparent dielectric. This layer would physically protect the metal finish as well as provide some thermal insulation between "hot" metal substrate and cold matrix film.

The second inventive embodiment involves propagation of light through a thin film without a metallic boundary and with a dielectric substrate which has an index of refraction greater than that of the thin film. Higher damage thresholds are possible by eliminating absorption by metallic surface. In this embodiment, reflective containment is achieved by careful launching of the light into the film along a direction closely parallel to the substrate. A beam propagating in the film with electric polarization parallel to the substrate, and incident at an 87 degree grazing angle, upon, for example, a rare gas-sapphire interface has a reflection coefficient of 79 percent. If one injected such a beam deviating by only three degrees from being parallel to the sapphire substrate then a 6 mm propagation length may be achieved with only two reflections on the rare gas-sapphire interface. About 60 percent of the laser beam will propagate 6 mm. Although such transmission lengths are clearly of no interest to those designing long distance optical information transmission systems, they do increase the interactive distance in matrix isolation spectroscopy by at least a factor of 60 and hence, are effectively used in the inventive technique.

Figure 3:
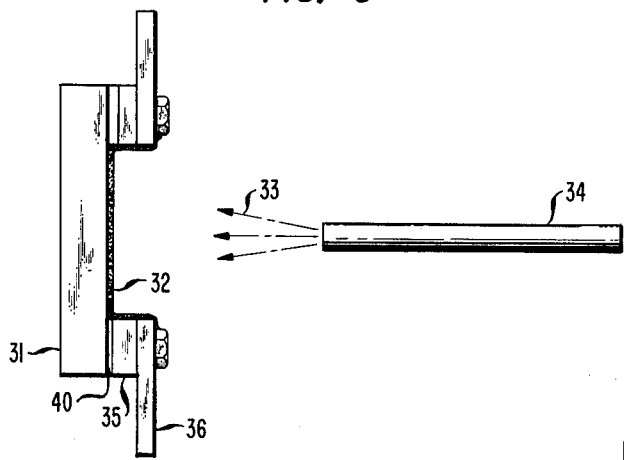
FIG. 3 is a specific embodiment of the inventive technique.

In both of the suggested inventive embodiments, it is advantageous to provide a smooth thin film face perpendicular to the substrate so as to permit efficient launching of all the light into the thin film. Two embodiments are suggested for the fabrication of such a perpendicular face. FIG. 3 is one such specific embodiment. In this figure, 31 is a dielectric substrate (for example, sapphire) upon which a thin film of guest-host material 32 is deposited. Deposition proceeds by maintaining the substrate 31 at a low temperature and directing a stream of gaseous guest-host material 33 toward the substrate by means of a deposition device 34. 35 is a slotted shield which acts as a barrier to deposition. 36 is an additional deposition barrier. Although the thickness of the film 32 is shown to be greater than that of the slot 40, the invention may be equally well-practiced when the film 32 is thinner than the thickness of the slot 40.

Figure 4:
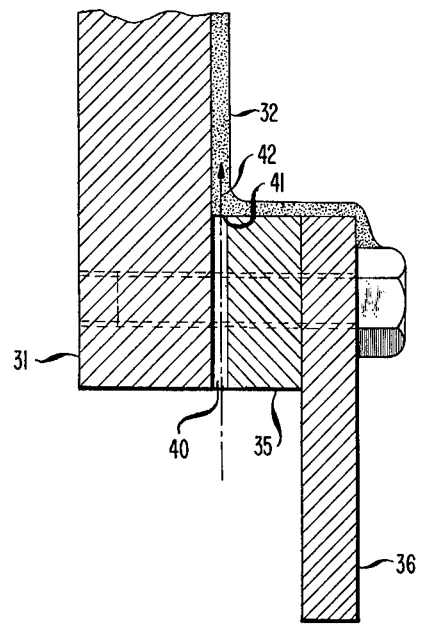
FIG. 4 is a detail of the technique of FIG. 3.

The slotted region 35 in FIG. 3 is shown in magnification in FIG. 4. In this figure, 31 is the substrate, 32 is the frozen thin film gas sample, while 35 is the slotted barrier with slot 40. Note that the physical characteristics of the gas, as well as the configuration of the barrier 35 yield a thin frozen film with an essentially flat perpendicular surface 41. Appropriate radiation 42 may then be transmitted through the slot 40 to enter the frozen gas sample 32 without significant scattering or change in direction of propagation, in part because of the essentially flat surface 41. The configuration of FIGS. 3 and 4 thereby permits the formation of a thin film particularly well suited to the insertion of electromagnetic radiation into the thin film at an angle parallel to the substrate, i.e., essentially perpendicular to the thin dimension of the film. Such insertion of radiation may result in transmission of the radiation through the thin film over distances greater than a centimeter. Radiation scattered perpendicular to the direction of transmission of the injected radiation may be then studied, or alternatively, light transmitted through the film may be analyzed, both to further study the characteristics of the guest material in the thin film.

Figure 5:
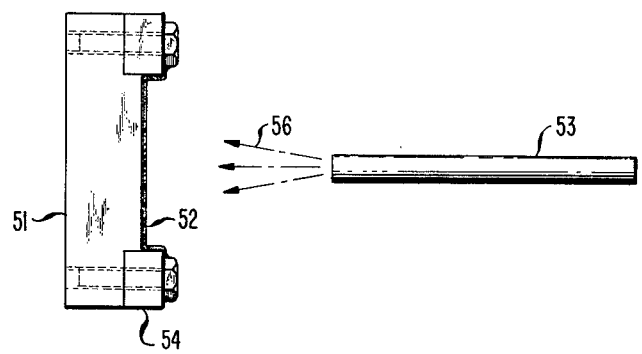
FIG. 5 is an alternative embodiment of the inventive technique.

FIG. 5 is an alternative embodiment which may be used to form a film with a smooth face perpendicular to the substrate. In the embodiment of FIG. 5, 51 is a substrate upon which the thin film is deposited. As in the previous figures, 52 is an appropriate thin film frozen on the substrate by means of a gaseous deposition device 53 which deposits material 56. In this embodiment, however, 54 is a sapphire block which is transparent to the analyzing radiation 55. Although the film 52 is shown in the FIG. to be less than the protruding height of the sapphire slot 40, the invention may be practiced with films thicker than that shown including films as thick as the protruding dimension of the block 54.

Figure 6:
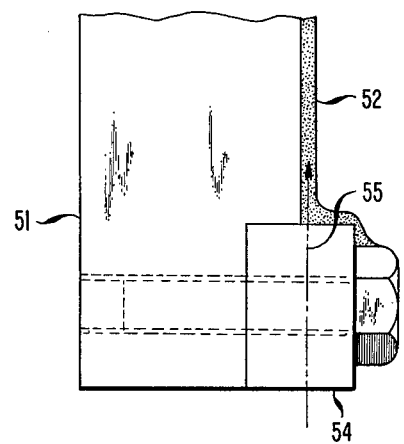
FIG. 6 is a detail of the specific embodiment of FIG. 5.

FIG. 6 is a magnification of the critical region of the film shown in FIG. 5. In FIG. 6, 51 is the substrate which is usually polished and which may be made, for example, of copper. 54 is the sapphire block. Note that the polished substrate surface 51 and the sapphire block 54 form approximately a right angle. The frozen gas is then deposited on the substrate to yield a film 52. By virture of the configuration of the substrate and the sapphire block, the gas freezes to form a film with a perfect perpendicular face. The sapphire is transparent to the impinging radiation 55 which then may enter the film with only the normal reflective loss at the sapphire-frozen gas interface.

Although the technique has been described in a somewhat limited sense, various parameters may be altered within the spirit of the invention. For example, the wavelength of the light propagated through the thin film can vary over a wide range, generally between 1000 Angstroms and 20 microns. The light may be coherent or incoherent. If the substrate boundary involves two dielectrics, there need be no limitation on the nature of the dielectric material within the spirit of the invention. For example, material such as sapphire, quartz, silicon, germanium, diamond, magnesium fluoride and sodium fluoride may be used. Alternatively, reflective surfaces may be used at the thin film boundary such as appropriate metals, perhaps deposited, including platinum, silver, gold, aluminum, rhodium, and nickel. Non-metallic reflecting surfaces such as commercial dielectric mirrors comprising multi-dielectric layers deposited on top of each other to maximize reflection in specific wavelength ranges, may be used. The thin film is usually frozen on the substrate in most embodiments at temperatures less than 200 degrees Kelvin. The host material may be any atomic or molecular species and usually involves such species that are liquids or vapors at 300 degrees Kelvin. The guest to-host concentration ratio may be up to 1-to-1, but in some instances, will be less than 1-to-10. For spectroscopic studies, the guest-host ratio will usually be less than 1-to-100. Multiple guests may be used but there will usually be no more than three different guest materials simultaneously frozen in a thin film. Although there is no inherent limitation on the thickness of the thin film, it will usually be between one-half and 400 microns.

Although it may be more advantageous to propagate the lightbeam parallel to the substrate surface, effective propagation may be obtained when the lightbeam is as much as 5 degrees away from parallel in the case of dielectric substrates and between 20 degrees and 30 degrees away from parallel in the case of metallic substrates.

EXAMPLE 1

To demonstrate a signal increase, using the inventive technique, we incorporate a luminescent molecule (p-benzoquinone-d4) into the matrix at 1/5000 relative concentration, and collect molecular emission with an optical system chosen to view emission from a line source with equal efficiency as from a point source. The analyzing system, a one meter spectrometer followed by a 2 inch end-on photomultiplier, views a 300 micron by 15 millimeter rectangular area with constant efficiency, if we neglect vignetting in the simple one element collection lens. The film and the optics are configured relative to the spectrometer so that an image is formed along the length of the spectrometer slit.

As mentioned above, a fundamental experimental problem involves achieving highly efficient laser coupling into the thin film matrix. In this experiment, the configuration of FIGS. 3 and 4 was utilized to achieve such highly efficient coupling. The gaseous sample was deposited onto an aluminum (or silver) mirror shown in the figure as 31. The mirror is masked by a copper bar having machined 50 and 100 micron slots. As shown in the figure, the side with the slots faces the flat mirror and a narrow empty volume is created just above the mirror in the region of the slot. As the sticking coefficient of the gases is near unity at 4 degrees Kelvin, a sharp matrix end will be created at the exit of the slot due to the masking effect of the copper bar just above the mirror surface. A second larger copper bar, 36, above the slotted bar helps to prevent gas deposition in the entrance to the slot. Injection of the optical radiation is achieved by focusing the beam through the empty slot and into the matrix film. In the experiment, a 6.5 mm propagation length through the matrix film was used followed by an identical output coupler.

As a light source, a Molectron DL200 dye laser was used, operating at 4809 Angstroms, and yielding $1 \times 10^{-4}$ joule pulses ($\Delta t$ approximately 8 nanoseconds), at a 10 Hz repetition rate. Various lenses were used to focus the beam to waists in the 80–75 micron region, corresponding to peak fluxes of approximately $2 \times 10^8$ to $4 \times 10^9$ watts per $cm^2$. These beam waist dimensions have been measured by passing the beam through a calibrated slit assembly. The quoted values correspond to the 50 percent transmission points. The laser beam, which does not have a $TEM_{00}$ transverse mode structure, remains in focus for several millimeters when focused to an 18 micron waist and for several centimeters at a focused waist of 75 microns. Matrices in the approximate thickness range of from 30 to 150 microns were investigated. Thickness were determined by comparing frozen gas thickness to the known heights of the machined slots. Pulsed gas depositions were employed with about 1 micron of thickness resulting from each additional pulse.

The deposition technique and resulting optical quality of the frozen gas layers are of critical importance. Neon gas forms an exceptionally clear homogeneous matrix when deposited at about 4.2 degrees Kelvin. If one observes the matrix as the 4809 Angstrom blue beam is focused into the entrance slot, one sees a perfectly collimated yellow luminescence line as the laser propagates through the matrix. If the initial matrix is optically clear, there is no perceptible beam divergence in the plane of the matrix and the injected beam retains the collimation given by the initial focusing lens. If there is a microscopic crack or an incorporated dust particle in the film, then deflection occurs. In order to obtain a long path length with a beam focused to a 75 micron waist, the exit coupler was removed to allow for a total propagation length of 13 mm. The luminesence from this line source was found to be a factor of 34 stronger than luminescence collected when the same 75 micron beam was focused directly on the front surface of the matrix. In this comparison, the beam strikes the surface at a 50–60 degree angle close to Brewster's angle, as it would in a prior art matrix scattering experiment. In this situation, theoretical scattering enhancement is (L/2d) approximately 130. Experimental results are within a factor of 4 of this limit leading to the conclusion that in this 50 micron neon matrix one is experimentally able to inject and propagate in via reflective containment, a substantial fraction of the incident beam.

With this power level, we are close to the damage threshold of the matrix. We find that matrix damage and propagation length are both correlated with laser polarization. If the light is polarized with electric vector parallel to the mirror-rate gas interface, then the laser beam propagates without damaging the matrix. With perpendicular polarization, propagation causes the matrix to immediately crack and blister along the laser pathway. Absorption of laser beam energy by the metallic surface is higher for perpendicular polarization. For example, we calculate that at a grazing 85 degree angle of incidence, 0.2 percent of a parallel polarized beam is absorbed in a reflection off a rare gas silver metal interface, while 1.4% of a perpendicularly polarized beam is absorbed. Our observations demonstrate that the laser power threshold for matrix damage is due to heating caused by absorption in the metallic mirror. Heating is less for parallel polarized modes and we have observed that we can increase the flux to approximately $4 \times 10^9$ w/cm$^2$ before occasional matrix damage occurs. We note that parallel polarization also maximizes incorporated molecule dipole scattering at right angles perpendicular to the substrate plane. We observe that on metallic mirror substrates reflective containment propagation has a higher threshold for laser damage than front surface illumination with the same beam waist. This observation apparently reflects increased metallic absorption at smaller angles of incidence on the rare gas-metal interface.

Of the rare gases neon, argon, krypton and xenon commonly used in matrix spectroscopy, neon normally gives the best guest molecular spectra, because of the very weak guest-host interaction. Unfortunately, the low cohesive energy of solid neon gives a low threshold for laser damage. We have found that argon has a higher damage threshold, but the greater cohesive energy of argon creates scattering problems. Argon matrices deposited either by slower continuous deposition or pulsed deposition near 4 degrees Kelvin are milky in appearance due to a microcrystalline local nature. A 100 micron argon matrix can appear to be opaque, and experimentally the propagation lengths in such samples are very small (less than 1 mm). Essentially, no luminescent scattering enhancement is observed. However, we are able to create relatively clear 50 micron argon matrices by pulsed deposition at 22 degrees Kelvin. In these samples, the beam propagates approximately 7 mm before a perceptible flaring is observed. A luminescence scattering enhancement of 9 was observed in this sample. Subsequently, we find that 28 degrees Kelvin pulsed deposition gave argon matrices of essentially equal optical quality to neon matrices.

EXAMPLE 2

The coupling device of FIGS. 5 and 6 were used in this Example. We insure that the end of the gas film will be optically flat and perpendicular to the propagation direction by freezing gas into a corner formed by a sapphire bar (the input coupler) and a raised copper surface. The laser propagates through the sapphire bar and just above the polished copper surface. Our device has a 7.5 mm propagation length followed by a second sapphire bar designed to act as an output coupler. With this arrangement, we observe luminescent scattering enhancements of 8-12 with 50-100 micron neon matrices. Recalling the fact that we only have one-half the propagation length used in the slot experiments, we conclude that the injection efficiency with this arrangement is within a factor of 2 of the slot coupler.

What is claimed is:
1. A method comprising
    directing a stream of a guest-host gaseous mixture to a cold substrate upon which the mixture freezes to yield a film of the frozen gaseous mixture on the substrate;
    directing a beam of electromagnetic energy through the frozen film;
    the improvement comprising
    the substrate is selected from the group consisting of dielectrics having a refractive index greater than that of the frozen gaseous film, and metals, and in that the electromagnetic energy is propagated through the film along a direction substantially parallel to the substrate and wherein,
    prior to directing the stream of the gaseous mixture to the cold substrate upon which it freezes, a slotted structure is placed on at least one end of the substrate,
    a passageway, parallel to the substrate surface, being formed, and bounded, by the slot in the said structure and the substrate,
    the said gaseous mixture, upon freezing, forming a thin film face, which covers at least part of the passageway exit, which face is perpendicular to the substrate,
    such that light, directed through the passageway entrance, which is opposite to that of the thin film face, passes through the passageway and enters the thin film.

2. The method of claim 1 further comprising detecting the electromagnetic energy emitted by or transmitted by the film.

3. The method of claim 1 wherein the thin film material and the wavelength and intensity of the propagated light are such that a chemical reaction occurs in the film.

4. The method of claims 2 or 3 wherein the beam of electromagnetic energy is coherent.

5. The method of claim 4 wherein the coherent electromagnetic energy has a wavelength between 1000 Angstroms and 20 microns.

6. The method of claim 1 wherein the substrate material which the thin film contacts is selected from the group consisting of sapphire, quartz, silicon, germanium, diamond, magnesium fluoride and sodium fluoride.

7. The method of claim 1 wherein the metal, i.e., material which the thin film contacts is selected from the group consisting of platinum, silver, gold, aluminum, rhodium and nickel.

8. The method of claim 1 wherein the substrate material which the thin film contacts is a non-metallic reflecting surface.

9. The method of claims 6, 7, or 8 wherein the temperature of the thin film is less than 200 degrees Kelvin.

10. The method of claim 1 wherein the host material is a liquid or a vapor at 300 degrees Kelvin.

11. The method of claim 10 wherein the guest-host ratio is less than 1:1.

12. The method of claim 11 wherein the guest-host ratio is less than 1:10.

13. The method of claim 12 wherein the guest-host ratio is less than 1:100.

14. The method of claim 12 or 13 wherein the guest material consists of up to three different constituents.

15. The method of claim 1 wherein the thickness of the thin film is between ½ and 400 microns.

16. The method of claim 1 wherein the substrate material which the thin film contacts is a dielectric and wherein the beam of electromagnetic energy is transmitted through the thin film at an angle of less than 5 degrees relative to the substrate.

17. The method of claim 1 wherein the substrate material which the thin film contacts is a metal and wherein the beam of electromagnetic energy transmitted through the thin film at an angle less than 30 degrees relative to the substrate.

18. The method of claim 1 wherein the thin film comprises an optical memory.

* * * * *